United States Patent [19]
Buckberg

[11] Patent Number: 6,024,096
[45] Date of Patent: Feb. 15, 2000

[54] ANTERIOR SEGMENT VENTRICULAR RESTORATION APPARATUS AND METHOD

[76] Inventor: Gerald D. Buckberg, 13238 Riviera Ranch Rd., Los Angeles, Calif. 90049

[21] Appl. No.: 09/071,817

[22] Filed: May 1, 1998

[51] Int. Cl.[7] .............................. A61B 19/00; A61M 1/10
[52] U.S. Cl. ................................ 128/898; 623/3; 600/16; 600/37
[58] Field of Search ................................ 623/1, 2, 11, 66, 623/3; 128/897, 898; 600/37, 16

[56] References Cited

U.S. PATENT DOCUMENTS

| | | | |
|---|---|---|---|
| 3,279,464 | 10/1966 | Kline | 128/64 |
| 3,656,185 | 4/1972 | Carpentier | 3/1 |
| 3,874,388 | 4/1975 | King et al. | 128/334 |
| 3,983,863 | 10/1976 | Janke et al. | 128/1 R |
| 4,042,979 | 8/1977 | Angell | 3/1.5 |
| 4,055,861 | 11/1977 | Carpentier | 3/1.5 |
| 4,164,046 | 8/1979 | Cooley | 3/1.5 |
| 4,204,283 | 5/1980 | Bellhouse | 3/1.5 |
| 4,217,665 | 8/1980 | Bex et al. | 3/1.5 |
| 4,366,581 | 1/1983 | Shah | 3/1.5 |
| 4,602,911 | 7/1986 | Ahmadi et al. | 623/2 |
| 4,690,134 | 9/1987 | Snyders | 128/64 |
| 4,821,723 | 4/1989 | Baker, Jr. et al. | 128/419 D |
| 4,917,089 | 4/1990 | Sideris | 606/215 |
| 4,957,477 | 9/1990 | Lundback | 600/16 |
| 4,973,300 | 11/1990 | Wright | 600/37 |
| 5,041,130 | 8/1991 | Cosgrove et al. | 623/2 |
| 5,104,407 | 4/1992 | Lam et al. | 623/2 |
| 5,131,905 | 7/1992 | Grooters | 600/16 |
| 5,192,314 | 3/1993 | Daskalakis | 623/3 |
| 5,258,000 | 11/1993 | Gianturco | 606/151 |
| 5,425,744 | 6/1995 | Fagan et al. | 606/213 |
| 5,433,727 | 7/1995 | Sideris | 606/213 |
| 5,451,235 | 9/1995 | Lock et al. | 606/213 |
| 5,507,811 | 4/1996 | Koike et al. | 623/11 |
| 5,571,172 | 11/1996 | Chin | 623/1 |
| 5,607,471 | 3/1997 | Seguin et al. | 623/2 |
| 5,702,343 | 12/1997 | Alferness | 600/37 |
| 5,800,528 | 9/1998 | Lederman et al. | 623/3 |
| 5,813,975 | 9/1998 | Valenti | 600/37 |

OTHER PUBLICATIONS

J. Bohm, P. Goettel, K. Bittigau, H. Laube and W. Konertz Title: Endoventricular Patch Plasty for Restoration of Ventrcular Geometry and Pump Function in Ventricular Aneurysm Date: 1996 Z. Kardio., vol. 85, Supplement No. 4, pp. 43–46.

Marisa Di Donato, MD; Giuseppe Barletta, MD; Mauro Maioli, MD; Fabio Fantini, MD; Philippe Coste, MD; Michel Sabatier, MD; Francoise Montiglio, MD; and Vincent Dor, MD. Title: Early Hemodynamic Results of Left Ventricular Reconstructive Surgery for Anterior Wall Left Ventricular Aneurysm Date: 1992; pp. 886–890.

Marisa Di Donato, MD; Michel Sabatier, MD; Vincent Dor, MD; Anna Toso, MD; Mauro Maioli, MD; Fabio Fantini, MD Title: Akinetic Versus Dyskenetic Postinfarction Scar: Relation to Surgical Outcome in Patients Undergoing Endoventricular Circular Patch Plasty Repair Date: 1997 pp. 1569–1575.

(List continued on next page.)

*Primary Examiner*—Mickey Yu
*Assistant Examiner*—Dinh X. Nguyen
*Attorney, Agent, or Firm*—Lyon & Lyon LLP

[57] ABSTRACT

The symptoms of congenital heart failure are addressed in this surgical procedure for mounting a patch in the ventricle of the heart to reduce ventricular volume. Placement of the patch is facilitated by palpating a beating heart to identify akinetic, although normal appearing, tissue. The patch has an oval configuration facilitating return of the heart to a normal apical shape which enhances muscle fiber efficiency and a normal writhing pumping action. The patch includes a semi-rigid ring, and a circumferential rim to address bleeding. Patch placement is further enhanced by creating a Fontan neck and use of pledged sutures. Intraoperative vascularization and valve replacement is easily accommodated. Increased injection fraction, reduced muscle stress, improved myocardial protection, and ease of accurate patch placement are all achieved with this procedure.

12 Claims, 12 Drawing Sheets

OTHER PUBLICATIONS

Vincent Dor Title: Left Ventricular Aneurysms: The Endoventricular Circular Patch Plasty Date: 1997 pp. 123–130.

Vincnet Dor, MD; Marisa Di Donato, MD Title: Ventricular remodeling in coronary artery disease Date: 1997 pp. 533–537.

Adib D. Jatene, MD; Sao Paulo, SP,. Brazil Title: Left ventricular aneurysmectomy Date: 1985 pp. 321–331.

K. Emmrich; Z. Kardiol; Title: Contribution to the discussion of the lecture by J. Bohm, Berlin Date: 1996 pp. 47–48.

Vincent Dor Title: Reconstructive Left Ventricular Surgery for Post–Ischemic Akinetic Dilatation Date: 1997 pp. 139–145.

Vincent Dor Title: The Treatment of Refractory Ischemic Ventricular Tachycardia by Endoventricular Patch Plasty Reconstruction of the Left Ventricle Date: 1997 pp. 146–155.-

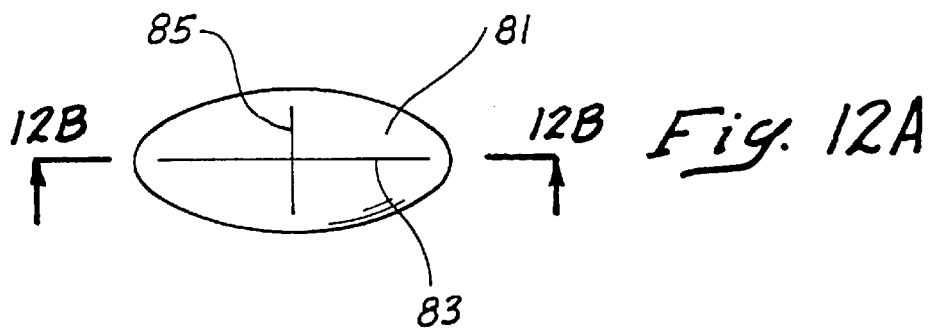
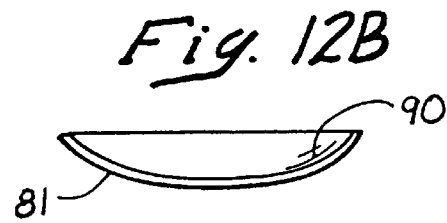
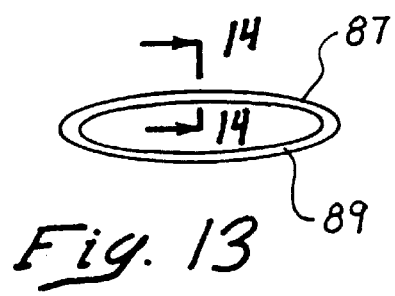
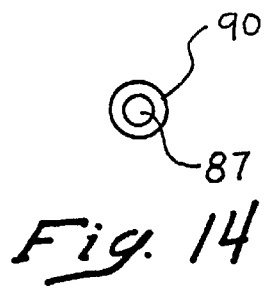
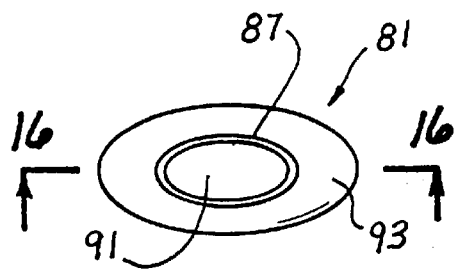

ANTERIOR SEGMENT VENTRICULAR RESTORATION APPARATUS AND METHOD

BACKGROUND OF THE INVENTION

1. Field of the Invention

This invention relates generally to surgical methods and apparatus for addressing ischemic cardiomyopathy, and more specifically to methods and apparatus for restoring the architecture and normal function of a mammalian heart.

2. Discussion of the Prior Art

The function of a heart in an animal is primarily to deliver life-supporting oxygenated blood to tissue throughout the body. This function is accomplished in four stages, each relating to a particular chamber of the heart. Initially deoxygenated blood is received in the right auricle of the heart. This deoxygenated blood is pumped by the right ventricle of the heart to the lungs where the blood is oxygenated. The oxygenated blood is initially received in the left auricle of the heart and ultimately pumped by the left ventricle of the heart throughout the body. It can be seen that the left ventricular chamber of the heart is of particular importance in this process as it is relied upon to pump the oxygenated blood initially through a mitral valve into and ultimately throughout the entire vascular system.

A certain percentage of the blood in the left ventricle is pumped during each stroke of the heart. This pumped percentage, commonly referred to as the ejection fraction, is normally about sixty percent. It can be seen that in a heart having a left ventricular volume such as seventy milliliters, an ejection fraction of sixty percent would deliver approximately 42 milliliters of blood into the aorta.

Realizing that the heart is part of the body tissue, and the heart muscle also requires oxygenated blood, it can be appreciated that the normal function of the heart is greatly upset by clotting or closure of the coronary arteries. When the coronary arteries are blocked, an associate portion of the heart muscle becomes oxygen-starved and begins to die. This is clinically referred to as a heart attack. Ischemic cardiomyopathy typically occurs as the rest of the heart dilates in an attempt to maintain the heart's output to the body.

As the ischemic cardiomyopathy progresses, the various structures of the heart are progressively involved including the septum, the apex and the antero4ateral wall of the left ventricle. Within a particular wall, the blood starvation begins at the inside of the wall and progresses to the outside of the wall. It can be seen that addressing ischemic cardiomyopathy shortly after the heart attack can limit the detrimental effects to certain elements of the heart structure, as well as the inner most thicknesses of the walls defining those structures.

As a heart muscle is denied blood nourishment support) its ability to participate, let alone aid, in the cardiac pumping function, is greatly diminished and typically nil. Such muscle is commonly referred to as akinetic, meaning it does not move. In some cases the wall will form elastic scar tissue which tends to balloon in response to the pumping action. This muscle tissue is not only akinetic, in that it does not contribute to the pumping function, but it is in fact dyskinetic, in that it detracts from the pumping function.

Perhaps the most notable symptom of ischemic cardiomyopathy is the reduction in the ejection fraction which may diminish, for example, from a normal sixty percent to only twenty percent. This results clinically in fatigue, and inability to do stressfiil activities, that require an increase in output of blood from the heart. The normal response of the heart to a reduction in ejection fraction is to increase the size of the ventricle so that the reduced percentage continues to deliver the same amount of oxygenated blood to the body. By way of example, the volume of the left ventricle may double in size. Furthermore, a dilated heart will tend to change its architecture from the normal conical or apical shape, to a generally spherical shape. The output of blood at rest is kept normal, but the capacity to increase output of blood during stress (i.e., exercise, walkdng) is reduced. Of course, this change in architecture has a dramatic effect on wall thickness, radius, and stress on the heart wall. In particular, it will be noted that absent the normal conical shape, the twisting motion at the apex, which can account for as much as one half of the pumping action, is lost. As a consequence, the more spherical architecture must rely almost totally on the lateral squeezing action to pump blood. This lateral squeezing action is inefficient and very different from the more efficient twisting action of the heart. The change in architecture of the heart will also typically change the structure and ability of the mitral valve to perform its function in the pumping process. Valvular insufficiency can also occur due to dilatation.

Although the dilated heart may be capable of sustaining life, it is significantly stressed and rapidly approaches a stage where it can no longer pump blood effectively. In this stage, commonly referred to as congestive heart failure, the heart becomes distended and is generally incapable of pumping blood returning from the lungs. This further results in lung congestion and fatigue. Congestive heart failure is a major cause of death and disability in the United States where approximately 400,000 cases occur annually.

Following coronary occlusion, successful acute reprefusion by throbmbolsis, (clot dissolution) percutaneous angioplasty, or urgent surgery can decrease early mortality by reducing arrhythmias and cardiogenic shock. It is also known that addressing ischemic cardiomyopathy in the acute phase, for example with reperfusion, may salvage the epicardial surface. Although the myocardium may be rendered alinetic, at least it is not dyskinetic. Post-infarction surgical re-vascularation can be directed at remote viable muscle to reduce ischemia. However, it does not address the anatomical consequences of the akinetic region of the heart that is scarred. Despite these techniques for monitoring ischemia, cardiac dilation and subsequent heart failure continue to occur in approximately fifty percent of post-infraction patients discharged from the hospital.

Various surgical approaches have been taken primarily to reduce the ventricular volume. This is also intended to increase the ejection fraction of the heart. In accordance with one procedure, viable muscle is removed from the heart in an attempt to merely reduce its volume. This procedure, which is typically accomplished on a beating heart, has been used for hearts that have not experienced coronary disease, but nevertheless, have dilated due to leaking heart valves. Other attempts have been made to remove the scarred portion of the heart and to close the resulting incision. This has also had the effect of reducing the ventricular volume.

In a further procedure, a round, circular patch has been proposed for placement typically in the lateral ventricular wall. Unfortunately, providing the patch with a circular shape has allowed the dilated heart to remain somewhat enlarged with a thin and overstressed wall section. The exact placement of the patch has been visually determined using only a visual indication where the typically white scar tissue meets the typically red normal tissue. Location of the patch has been facilitated in a further procedure where a continuous suture has been placed around the ventricular wall to define a neck for receiving the patch. The neck has been formed in the white scar tissue rather than the soft viable muscle. This procedure has relied on cardioplegia methods to stop the beating of the heart and to aid in suture placement.

These surgical procedures have been met with some success as the ejection fraction has been increased, for example, from twenty-four percent to forty-two percent. However, despite this level of success, little attention has been paid to myocardial protection, the potential for monitoring the writhing action associated with apical structure, or the preferred structure for the patch. Failure to protect the heart during restoration of the segment has increased hospital mortality, morbidity, and irreversibly damaged some normal muscle needed to maintain the heart's output.

SUMMARY OF THE INVENTION

The procedure of the present invention is preferably performed on a beating heart. This is believed to greatly improve the myocardial protection during the restoration process. The procedure further benefits from the beating of the heart by providing a palpable indication of preferred patch placement. As opposed to prior procedures, the primary intent is to exclude, not only the budging dyskinetic segments, but also the non-contracting akinetic segments of the heart which do not contribute to the pumping action. As a result, akinetic segments, despite a normal visual appearance, can be included for removal in this procedure. The process may include an endoventriclar Fontan suture, but the stitch will typically be placed in normal tissue with palpable guidance rather than in scar tissue and only a visual determination.

A non-circular, anatomically-shaped, typically oval patch is proposed and may be formed of a sheet material such as mammalian fixed pericardium. The patch may include a continuous ring which separates the body of the material from a hemostatic rim or flange which facilitates bleeding control. The patch is fixed to the Fontan neck preferably using pledgeted, interrupted sutures to secure patch placement and avoid distortion. Closure of the excluded ventricle over the hemostatic patch avoids dead space and provides security against patch leaks and resulting expansion.

These and, other features and advantages of the invention will become more apparent with a description of preferred embodiments and reference to the associated drawings.

DESCRIPTION OF THE DRAWINGS

FIG. 12A is a plan view of sheet material included in one embodiment of the patch associated with the present invention;

FIG. 12B is a cross section view taken along lines 12B—12B of FIG. 12A and illustrating the sheet material in a concave configuration;

FIG. 13 is a top plan view of a ring associated with the patch of the present invention;

FIG. 14 is a circumferential cross section taken along lines 14—14 of FIG. 13;

FIG. 15 is a top plan view showing the sheet material and ring combined to form one embodiment of the patch of the present invention;

DESCRIPTION OF PREFERRED EMBODIMENTS AND BEST MODE OF THE INVENTION

Figure 1:
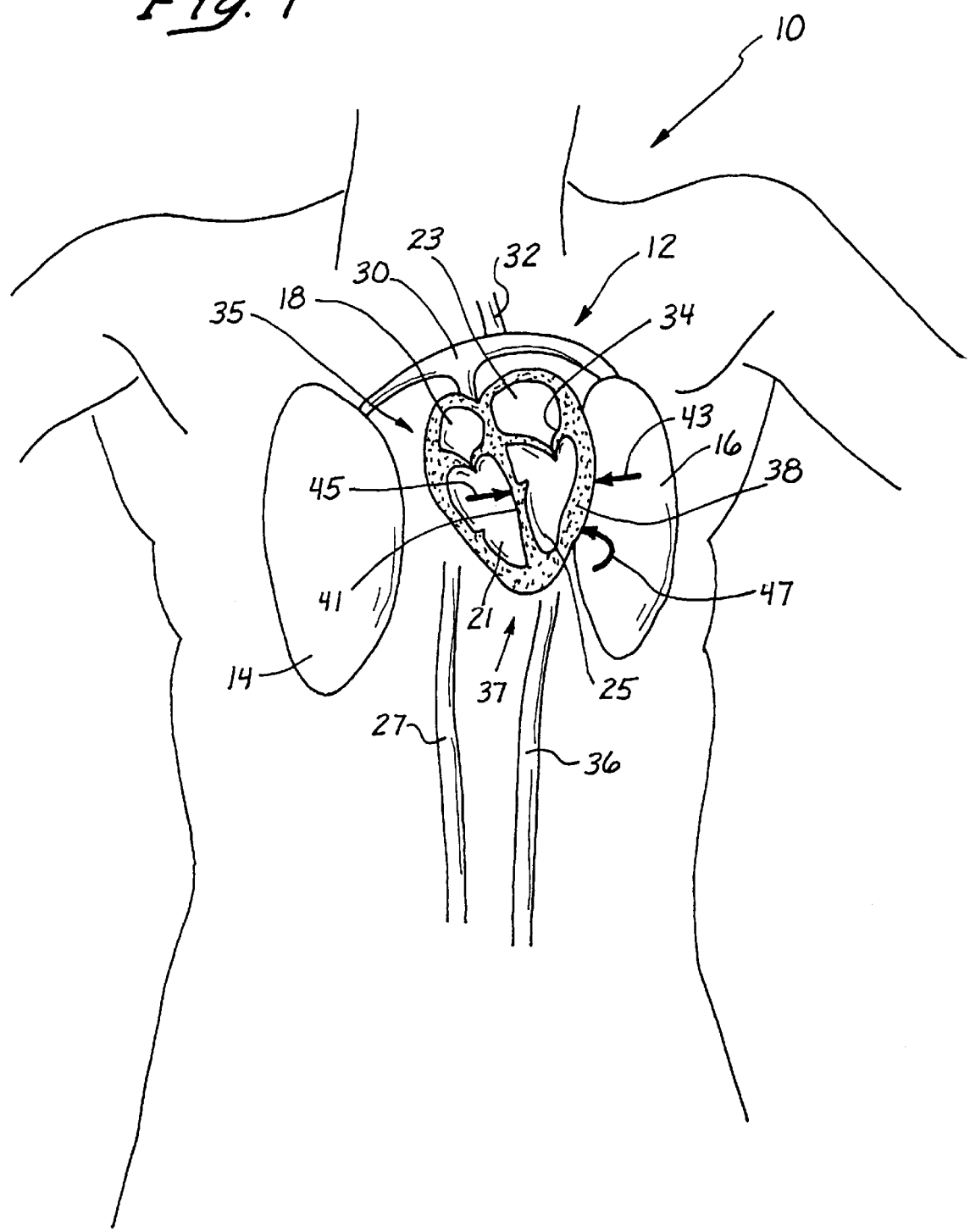
FIG. 1 is a perspective view of the abdominal cavity of a human body showing the heart in cross section.

Abdominal portions of the human body are illustrated in FIG. 1 and designated by the reference numeral 10. The body 10 is merely representative of any mammalian body having a heart 12 which pumps blood containing nutrients and oxygen, to vitalize tissue in all areas of the body 10. Other organs of particular importance to this blood circulation process include the lungs 14 and 16, and the vasculature of the body 10 including arteries which carry blood away from the heart 12 and veins which return blood to the heart 12.

The heart 12 typically includes four chambers, a right auricle 18, a right ventricle 21, a left auricle 23 and a left ventricle 25. In general, the auricles 18 and 23 are receiving chambers and the ventricles 21 and 25 are pumping chambers. Each of these chambers 18–25 is associated with a respective function of the heart 12. For example, it is the purpose of the right auricle 18 to receive the deoxygenated blood returning in the veins of the body 10, such as the femoral vein 27. From the right auricle 18, the deoxygenated blood passes into the right ventricle 21 from which it is pumped through a pulmonary artery 30 to the lungs 14 and 16.

Within the lungs 14 and 16, the deoxygenated blood is reoxygenated and returned to the left auricle 23 of the heart 12 through a pulmonary vein 32. From this chamber, the oxygenated blood passes through a mitral valve 27 into the left ventricle 25. With each beat of the heart 12, the left ventricle 25 contracts pumping the oxygenated blood into the arteries of the body, such as the femoral artery 36.

The shape of the normal heart 12 is of particular interest as it dramatically affects the way that the blood is pumped. It will be noted, for example, that the left ventricle 25, which is the primary pumping chamber, is somewhat elliptical, conical or apical in shape in that it is longer than it is wide and descends from a base 35 with a decreasing cross-sectional circumference, to a point or apex 37. The left ventricle 25 is further defined by a lateral ventricle wall 38, and a septum 41 which extends between the auricles 18, 23 and the ventricles 21, 25.

The pumping of the blood from the left ventricle 25 is accomplished by two types of motion. One of these motions is a simple squeezing motion which occurs between the lateral wall 38 and the septum 41 as illustrated by the arrows 43 and 45, respectively. The squeezing motion occurs as a result of a thickening of the muscle fibers in the myocardium. This compresses the blood in the ventricle chamber 25 and ejects it into the body 10. The thickening changes between diastole (before the heart is contracting) and systole (when the heart is ejecting). This is seen easily by echocardiogram, and can be routinely measured.

The other type of motion is a twisting or writhing motion which begins at the apex 37 and rises toward the base 35, as shown by the arrow 47. The rising writhing motion occurs because the heart muscle fibers run in a circular or spiral direction around the heart 12. When these fibers constrict, they cause the heart to twist initially at the small area of the apex 37, but progressively and ultimately to the wide area of the base 35. These squeezing and twisting motions are equally important as they are each responsible for moving approximately one-half of the blood pumped.

The amount of blood pumped from the left ventricle 25 divided by the amount of blood available to be pumped is referred to as the ejection fraction of the heart 12. Generally, the higher the ejection fraction the more healthy the heart. A normal heart, for example, may have a total volume of one hundred milliliters and an ejection fraction of sixty percent. Under these circumstances, 60 milliliters of blood are pumped with each beat of the heart 12. It is this volume of blood in the normal heart of this example, that is pumped with each beat to provide nutrients including oxygen to the muscles and other tissues of the body 10.

Figure 2:
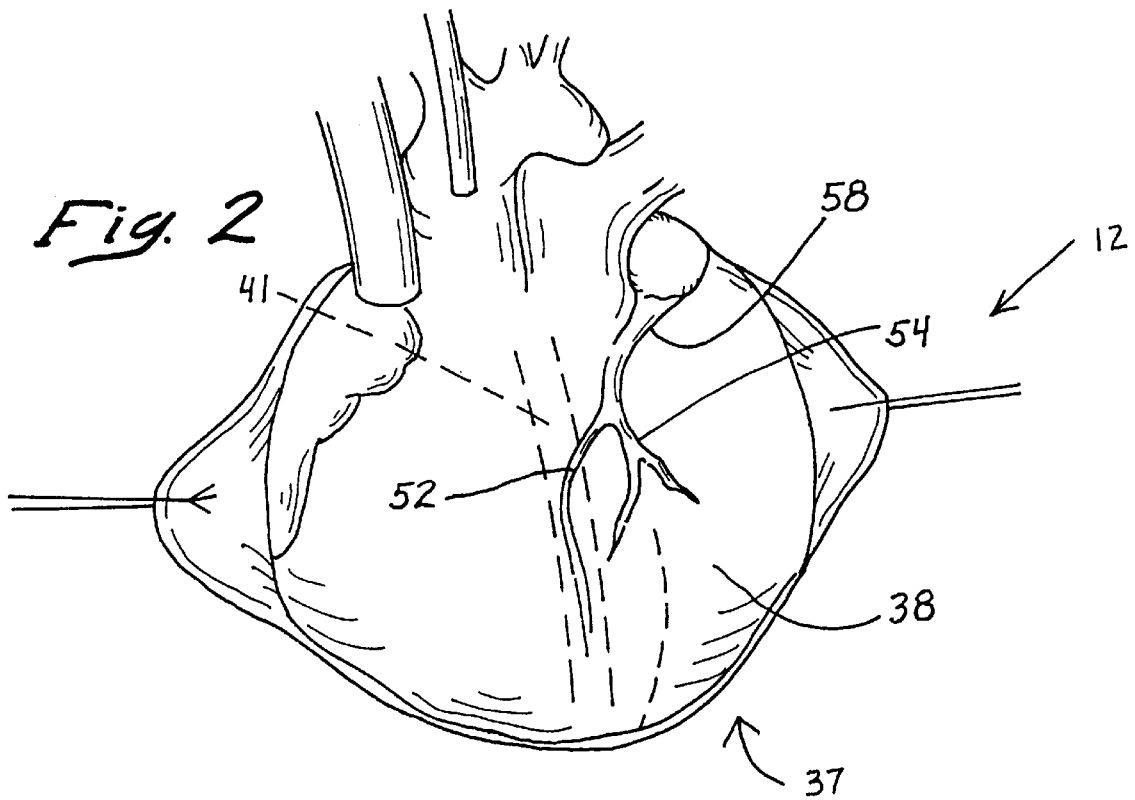
FIG. 2 is a front plan view of the heart showing coronary arteries which feed the septum, apex and lateral wall of the myocardium.

The muscles of the body, of course, include the heart muscle or myocardium which defines the various chambers 18–25 of the heart 12. This heart muscle also requires the nutrients and oxygen of the blood in order to remain viable. With reference to FIG. 2, it can be seen that the anterior or front side of the heart 12 receives oxygenated blood through a common, artery 58 which bifurcates into a septal artery branch 52, which is directed toward the septum 41, and an anterior descending artery 54 which is directed toward the apex 37 and the lateral ventricle wall 38.

When a blockage occurs in one of these coronary arteries, that portion of the heart muscle which is fed by the blocked artery no longer receives the oxygen needed to remain viable. These blockages typically occur in the common artery 58 and in the septal artery branch 52. When the common artery is involved, the septum 41, apex 37 and lateral wall 38 all become ischemic or oxygen deprived. When only the septal artery branch 52 is involved, the ischemic symptoms are limited primarily to the septum 41 and the apex 37. In this latter case, the septum 41 is almost always affected, the apex 31 is usually affected, and the lateral wall 38 is sometimes affected.

As the ischemia progresses through its various stages, the affected myocardium dies losing its ability to contribute to the pumping action of the heart. The ischemic muscle is no longer capable of contracting so it cannot contribute to either squeezing or the twisting motion required to pump blood. This non-contracting tissue is said to be akinetic. In severe cases the akinetic tissue, which is not capable of contracting, is in fact elastic so that blood pressure tends to develop a bulge or expansion of the chamber. This is particularly detrimental as the limited pumping action available, as the heart 12 loses even more of its energy to pumping the bulge instead of the blood.

Figure 3:
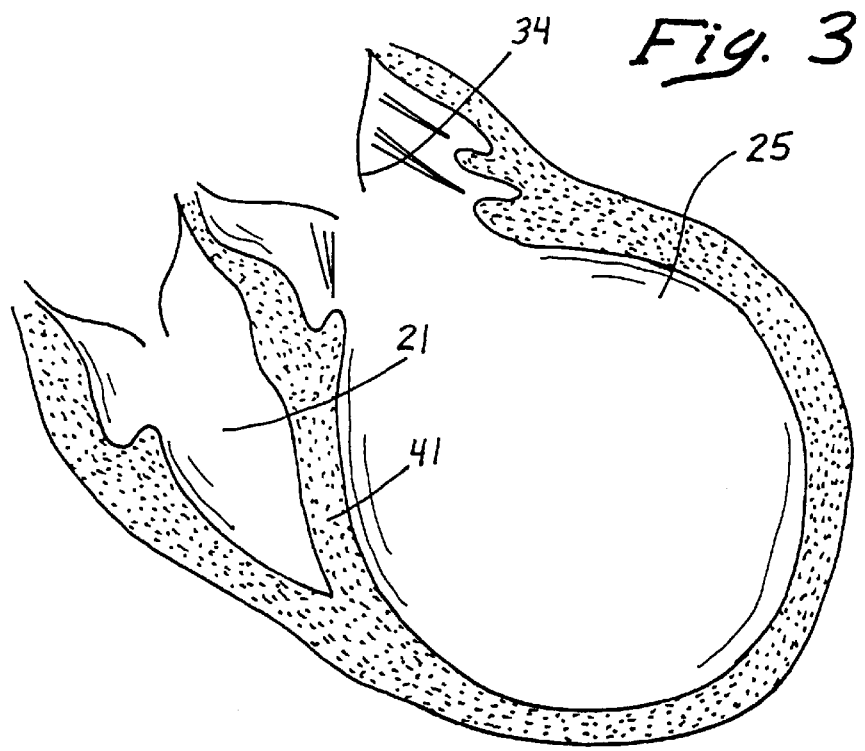
FIG. 3 is a axial cross section view of the ventricular portions of the heart illustrating a dilated, generally spherical left ventricle.

The body's reaction to ischemic infarction is of particular interest. The body 10 seems to realize that with a reduced pumping capacity, the ejection fraction of the heart is automatically reduced. For example, the ejection fraction may drop from a normal sixty percent to perhaps twenty percent. Realizing that the body still requires the same volume of blood for oxygen and nutrition, the body causes its heart to dilate or enlarge in size so that the smaller ejection fraction pumps about the same amount of blood. As noted, a normal heart with a blood capacity of seventy milliliters and an ejection fraction of sixty percent would pump approximately 42 milliliters per beat. The body seems to appreciate that this same volume per beat can be maintained by an ejection fraction of only thirty-percent if the ventricle 25 enlarges to a capacity of 140 milliliters. This increase in volume, commonly referred to as "remodeling" not only changes the volume of the left ventricle 25, but also its shape. The heart 12 becomes greatly enlarged and the left ventricle 25 becomes more spherical in shape losing its apex 37 as illustrated in FIG. 3. In this view, the stippled area of cross section shows the ischemic or infracted region of the myocardium.

On the level of the muscle fibers, it has been noted that dilation of the heart causes the fibers to reorient themselves so that they are directed away from the inner heart chamber containing the blood. As a consequence, the fibers are poorly oriented to accomplish even the squeezing action as the lines of force become less perpendicular to the heart wall. It will be noted that this change in fiber orientation occurs as the heart dilates and moves from its normal elliptical shape to its dilated spherical shape. The spherical shape further reduces pumping efficiency since the fibers which normally encircle the apex to facilitate writhing are changed to a more flattened formation as a result of these spherical configurations. The resulting orientation of these fibers produce lines of force which are also directed laterally of the ventricle chamber 25. Thus, the dilation and resulting spherical configuration greatly reduces contraction efficiency.

Although the remodeling of the heart 12 by the body 10 helps in maintaining the blood flow, it places the heart wall under considerable stress which eventually can result in congestive heart failure. While myocardial ischemia or infarction is the primary cause of death and disability in this country, congestive heart failure is certainly the secondary cause with over 400,000 cases reported annually. It is this post-infarction congestive heart failure which is a primary focus of the present invention.

As noted, successful acute reprefusion by thrombolysis, percutaneous angioplasty, or urgent surgery can decrease early mortality by reducing arrhythmia and cariogenic shock. These procedures applied in the early stages of ischemia can also aid in salvaging the epicardial surface of the myocardium and thereby prevent akinetic tissue from becoming dyskinetic. Notwithstanding these known methods of intervention, cardiac dilation and subsequent congestive heart failure occur in approximately fifty percent of the post-infraction patients.

The procedure of the present invention addresses the effects of myocardial infarction using a cardioprotective approach to restore the geometry of the left ventricle. This is not a "remodeling" procedure automatically produced by the body 10, nor a "reconstructive" procedure which leaves the heart with other than a normal geometry. Rather, this is a procedure which attempts to "restore" the normal geometry, and particularly the apical configuration of the left ventricle 25. The procedure reduces the volume of the left ventricle 25, but also increases the percentage of the ventricle wall which is viable. This greatly increases the ejection fraction of the heart and significantly reduces heart stress.

With a primary purpose of reducing the left ventricle volume, the intent of the procedure initially is to remove that portion of the wall which is not capable of contracting. This, of course, includes the scarred dyskinetic segments, which are easy to visualize, but may also include akinetic segments, which do not contract despite their normal appearances.

Figure 4:
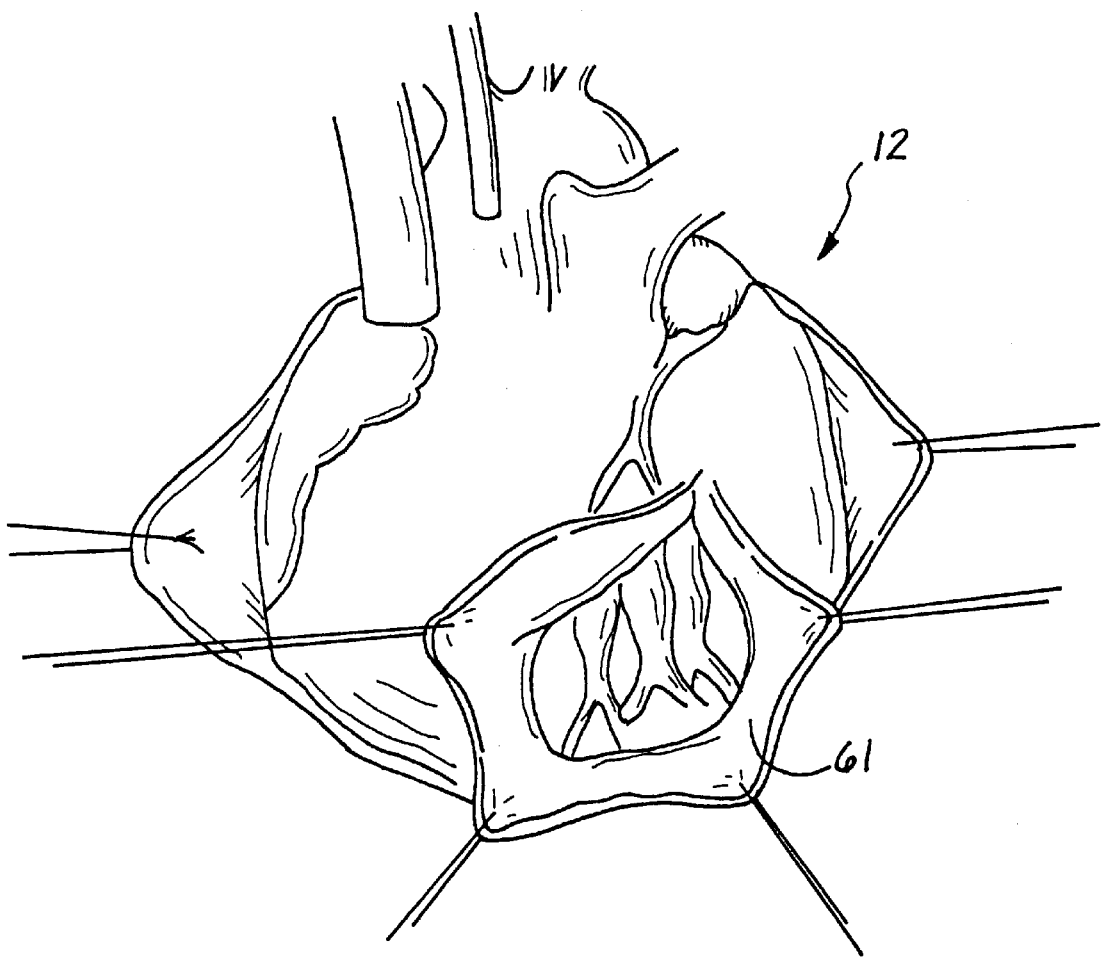
FIG. 4 is an anterior elevation view of the heart with an incision into the left ventricle through dyskinetic scar tissue.

An incision 61 is cut into the myocardial wall of the dilated heart 12 as illustrated in FIG. 4. If the surrounding tissue is dyskinetic, it will typically be formed entirely of thin, elastic scar tissue. It is the elasticity of this scar tissue which causes the detrimental ballooning or bulging effects previous discussed.

Figure 5:
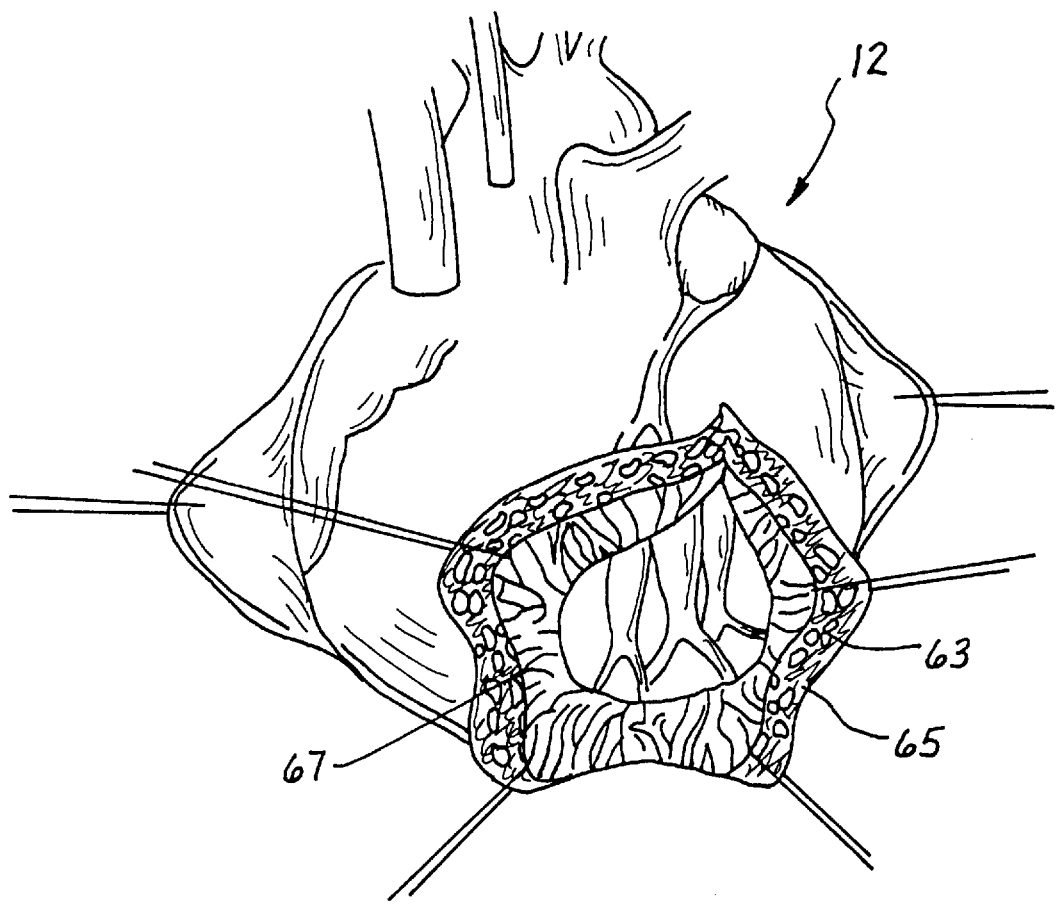
FIG. 5 is an anterior elevation view similar to FIG. 4 where the incision is made in marbled akinetic tissue.

In some cases, the tissue surrounding the incision 61 will be somewhat marbled as illustrated in FIG. 5 with patches of both scar tissue 63 and viable red tissue 65. This marbled tissue is often characterized by trabeculae 67 which form ridges along the inner surface or endothelium of the wall. In spite of the presence of some viable tissue 65, these marbled walls of the heart 12 may nevertheless be akinetic.

Figure 6:
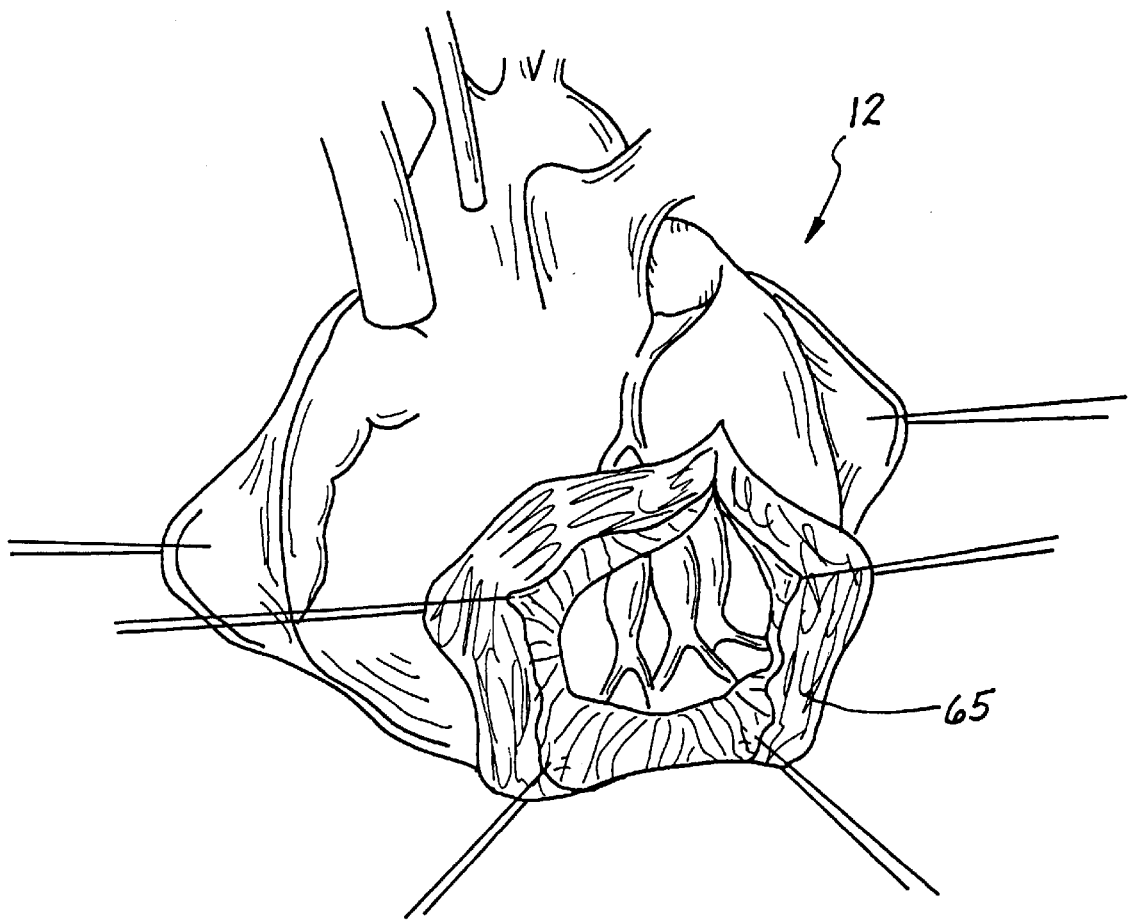
FIG. 6 is an anterior elevation view similar to FIG. 5 illustrating the incision made in normal-looking akinetic tissue.
Figure 8:
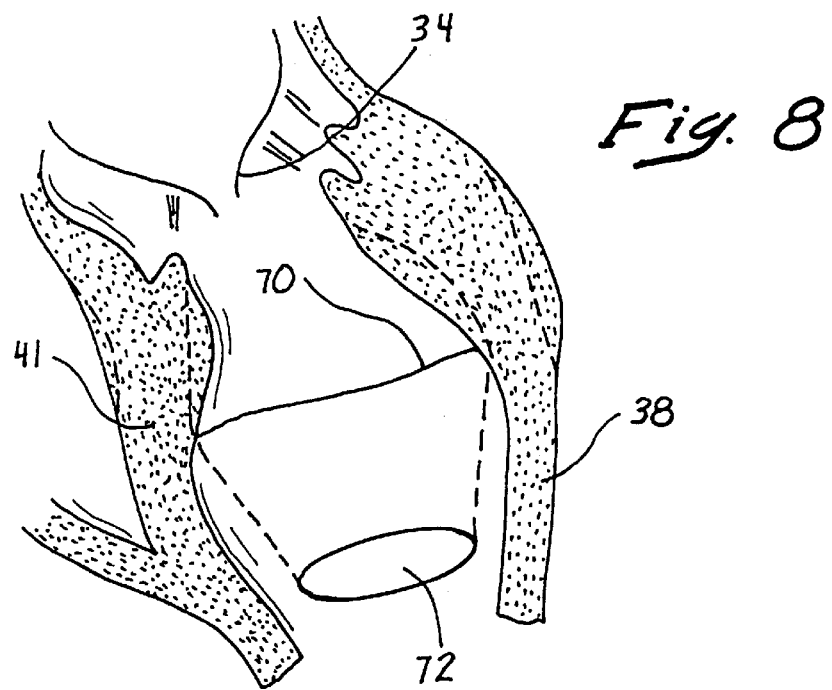
FIG. 8 is a axial cross section view similar to FIG. 7 illustrating the palpating heart and a preferred zone of placement for a patch associated with the present invention.

With reference to FIG. 6, it is apparent that the akinetic portion of the myocardium may even appear to be viable with an absence of white scar tissue and the presence of a full red color. Nevertheless, these portions are akinetic and offer no positive effect to the pumping process.

Figure 7:
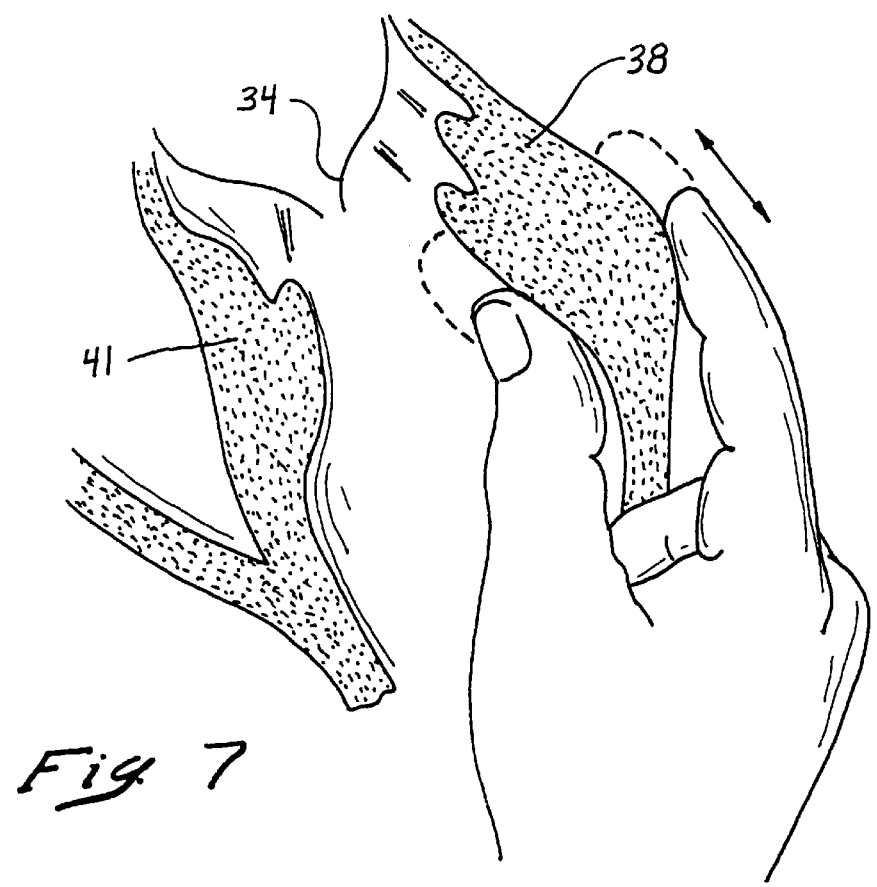
FIG. 7 is a axial cross section view of the left ventricle showing the surgeon's hand palpating the myocardium to define an imaginary circumferential line of separation between viable and akinetic tissue.

Given these factors, it is apparent that a determination as to where the akinetic portions begin and end cannot be a visual determination as relied on by the prior art. Although the visual appearance may be of some value in this determination, ultimately, one must palpate the tissue as illustrated in FIG. 7. Note that this emphasizes the importance of performing the restorative surgery on a beating heart. By palpating the myocardial wall, one can feel where the contractions of the lateral ventricular wall 38 and the septum 41 begin and end. Without regard for color or other properties visually distinguishable, the palpating will usually indicate viable tissue on one side of an imaginary circumferential line 70, with akinetic and dyskinetic tissue on the other side of the imaginary line 70. As described in greater detail below, a patch 72 will ultimately be positioned relative to this imaginary circumferential line 70 not only to reduce the volume of the left ventricle 25 but also to define that reduced volume with a larger percentage of viable heart muscle.

Figure 9:
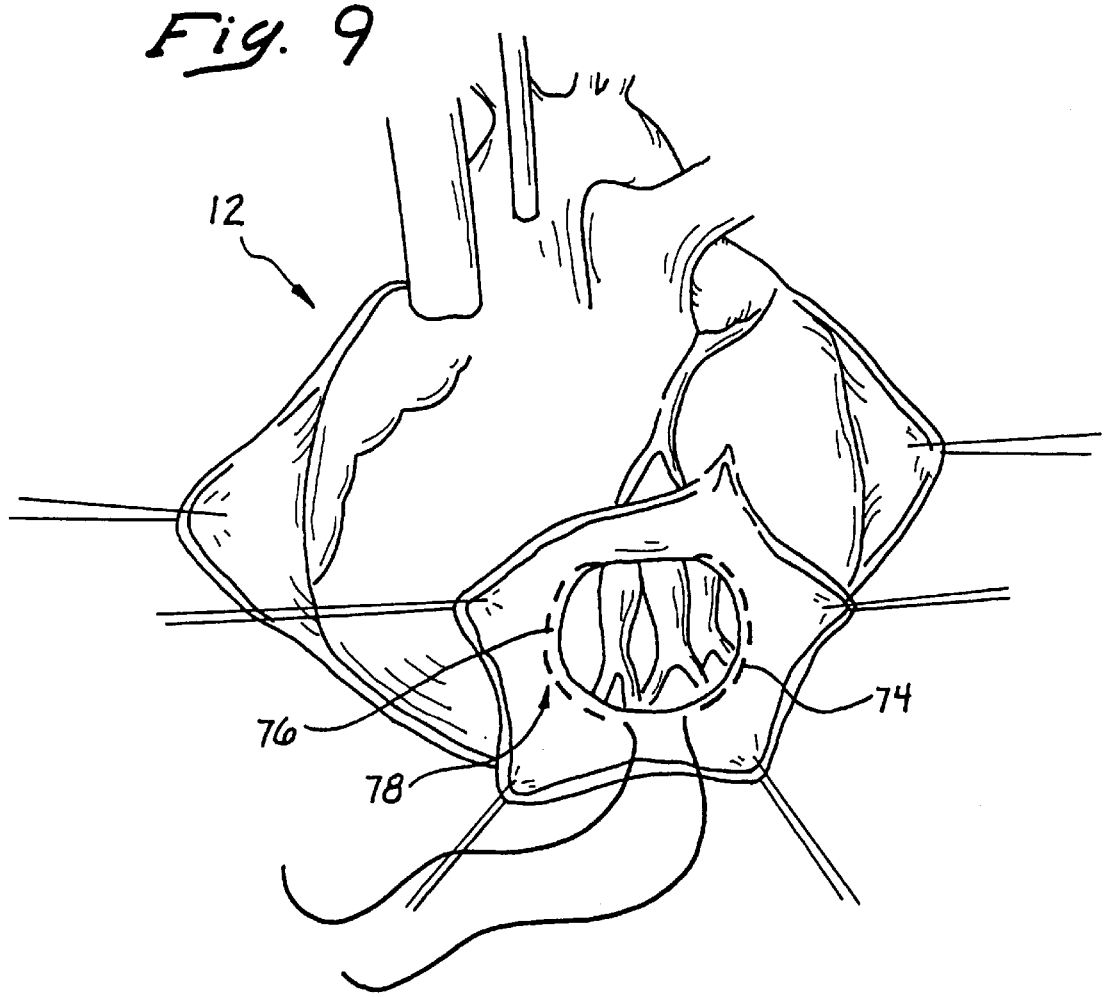
FIG. 9 is an anterior elevation view similar to FIG. 4 and illustrating placement of a Fontan stitch in the ventricular wall.
Figure 10:
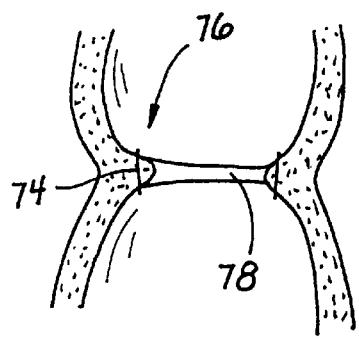
FIG. 10 is an axial cross section view illustrating a Fontan neck created by the Fontan stitch.
Figure 11:
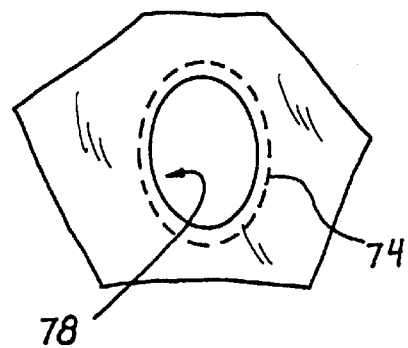
FIG. 11 is a side elevation view of the opening illustrated in FIG. 9 with the Fontan suture tightened to facilitate the natural oval formation of the opening.

After the preferred location of the patch 72 has been determined relative to the circumferential line 70, a continuous Fontan stitch 74 can be placed in proximity to the line 70 as illustrated in FIG. 9. This stitch 74 produces an annular protrusion 76 which forms a neck 78 relative to the imaginary line 70. This neck 78 initially may have a round circular configuration as illustrated in FIG. 9. However, as the suture 74 is tightened, the musculature of the myocardium will form a natural oval shape as illustrated in FIG. 11. It is this oval-shaped neck 78, formed by the Fontan stitch 74, which in its natural ovoid shape is particularly adapted to receive the patch 72 of the present invention.

Providing the patch 72 with a configuration complimentary to the ovoid shape of the Fontan stitch 74 is believed to be of particular importance and advantage to the present invention. In the past, patches of a round, circular form were used. This form maintained the dilatation of stretch fibers in their more inefficient transverse orientation. As a result, the fiber contraction continued to be very inefficient. Providing the patch 72 with an oval configuration restores the apex 37 or elliptical form of the heart 12. On a muscle fiber level, the fibers are directed back to a more normal, meaning generally perpendicular, orientation with respect to the heart wall 38. This reorients the lines of contraction force to greatly increase the contraction efficiency.

Construction of various embodiments of the patch 72 are discussed with reference to FIGS. 12A–20. In the plan view of FIG. 12A, a sheet material 81 is illustrated to have the-shape of an ellipse with a major axis 83 between 30 and 50 millimeters and a minor axis 85 between 20 and 30 millimeters. It is contemplated that the sheet material 81 can be provided in two sizes, such as 20×30 millimeters and 30×40 millimeters.

The sheet material 81 may be formed, for example, from Dacron (Hemashield), or polytetrafluroethylene (Gortex). However in a preferred embodiment, the sheet material 81 is formed of autologous pericardium,or some other fixed mammalium tissue such as bovine or porcine pericardium. Importantly, the sheet material 81 is preferably sized and configured with a shape similar to that of the Fontan neck 78 as illustrated in FIG. 11. As noted, this shape is non-circular and preferably oval.

The sheet material 81 can have a generally flat planar configuration, or can be shaped as a section of a sphere. The spherical shape can be achieved as illustrated in FIG. 12B by fixing the pericardium while it is stretched over a spherical die to form a concave surface 90.

In addition to the sheet material 81, the patch 72 also preferably includes a ring 87 which will typically have a toroidal configuration with a circumferential cross section that is circular, as shown in FIG. 13. The ring will typically be formed of a plastic graph material that can also be made of curled autogenous tissue such as fascia or pericardium. In general, the ring 87 can be formed from any biocompatible material having a degree of flexibility suitable to prevent interference with the normal contractions of the heart 12.

The circumferential cross section view of FIG. 14 illustrates that the ring 87 may be enclosed in a tubular sheath 90 which may be formed from woven Dacron, and incorporated to promote tissue ingrowth to the patch 72.

Figure 16:
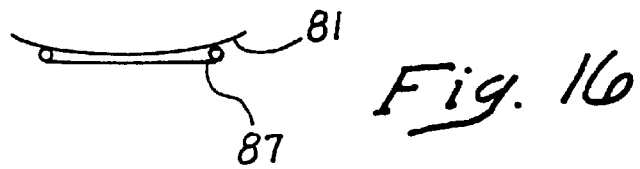
FIG. 16 is a cross section view of the patch taken along lines 16—16 of FIG. 15.

The ring 87 will generally have a non-circular shape which may be similar to but smaller than the shape of the material 81. Providing the ring 87 with a shape similar to the material 81 will enable the ring 87 to be attached to the material 81 as illustrated in FIGS. 15 and 16 with a body 91 of the patch disposed within the ring 87, and a circumferential rim or flange 93 disposed outwardly of the ring 87. The rim 93 will preferably have a constant width around its circumference. This width will typically be in a range between 5 and 8 millimeters.

Figure 17:
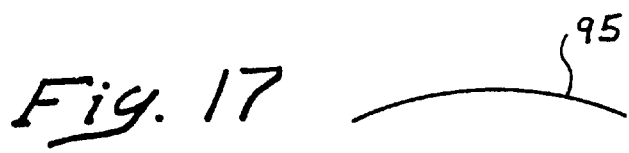
FIG. 17 is a cross section view similar to FIG. 12B and illustrating the sheet material in a convex configuration.
Figure 18:
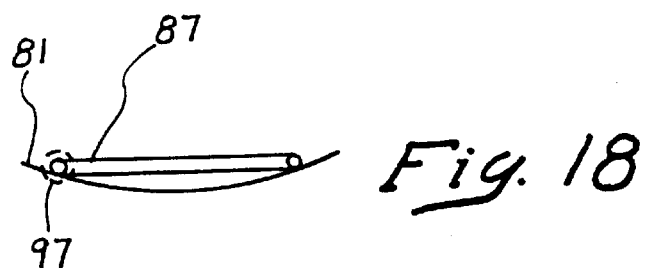
FIG. 18 is a cross section view similar to FIG. 16 and illustrating the ring disposed on a concave surface of the sheet material.

Many variations on the patch 72 will be apparent from the foregoing discussion. For example, as illustrated in FIG. 17, the sheet material 81 can be provided with a convex surface 95 facing the left ventricle 25 rather than the concave surface illustrated in FIG. 13. As illustrated in FIGS. 16 and 18, the ring 87 can be disposed on either the interior or exterior side of the material 81.

Figure 19:
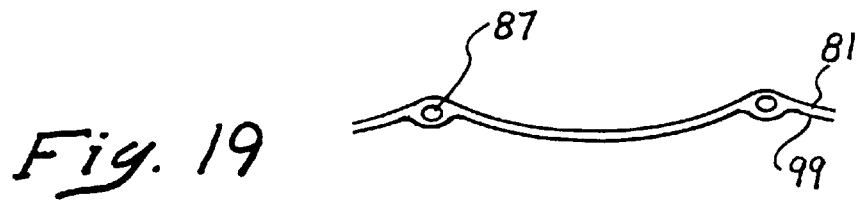
FIG. 19 is a cross section view similar to FIG. 18 and illustrating the ring sandwiched between two pieces of the sheet material.
Figure 20:
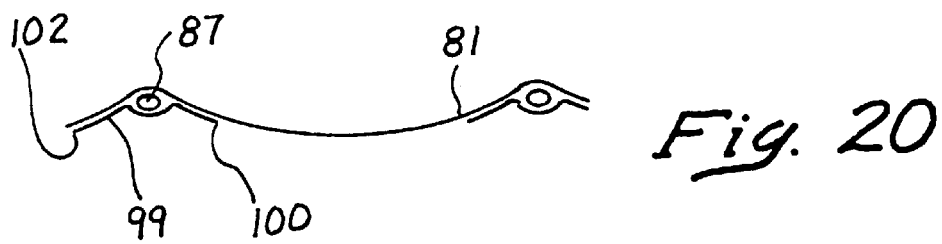
FIG. 20 is a cross section view similar to FIG. 19 and illustrating the ring sandwiched between two pieces of material, but having only a single layer in the center of the patch.

With reference to FIG. 18, the ring 87 can be attached to the material 81 by adhesive or by stitches 97 passing over with the reference to FIG. 19 ring 87 and through the material 81. Alternatively, the ring 87 can be sandwiched between two pieces of the sheet material. In this case, a second piece of the sheet material 99 can be positioned on the side of the ring 87 opposite to the sheet material 81. Appropriate sutures extending around the ring 87 and through the materials 81 and 99 will sandwich the ring and maintain it in the preferred position. With reference to FIG. 20, the second piece of material 99 can be formed as a circle with an inner diameter 100 less than that of the ring 87, and a outer diameter 102 generally equal to that of the material 81.

It will be appreciated that many variations on these preferred embodiments of the patch 82 will be apparent each having a generally non-circular sheet material, such as the material 81, and perhaps a somewhat flexible toroid or oval ring 87.

Figure 21:
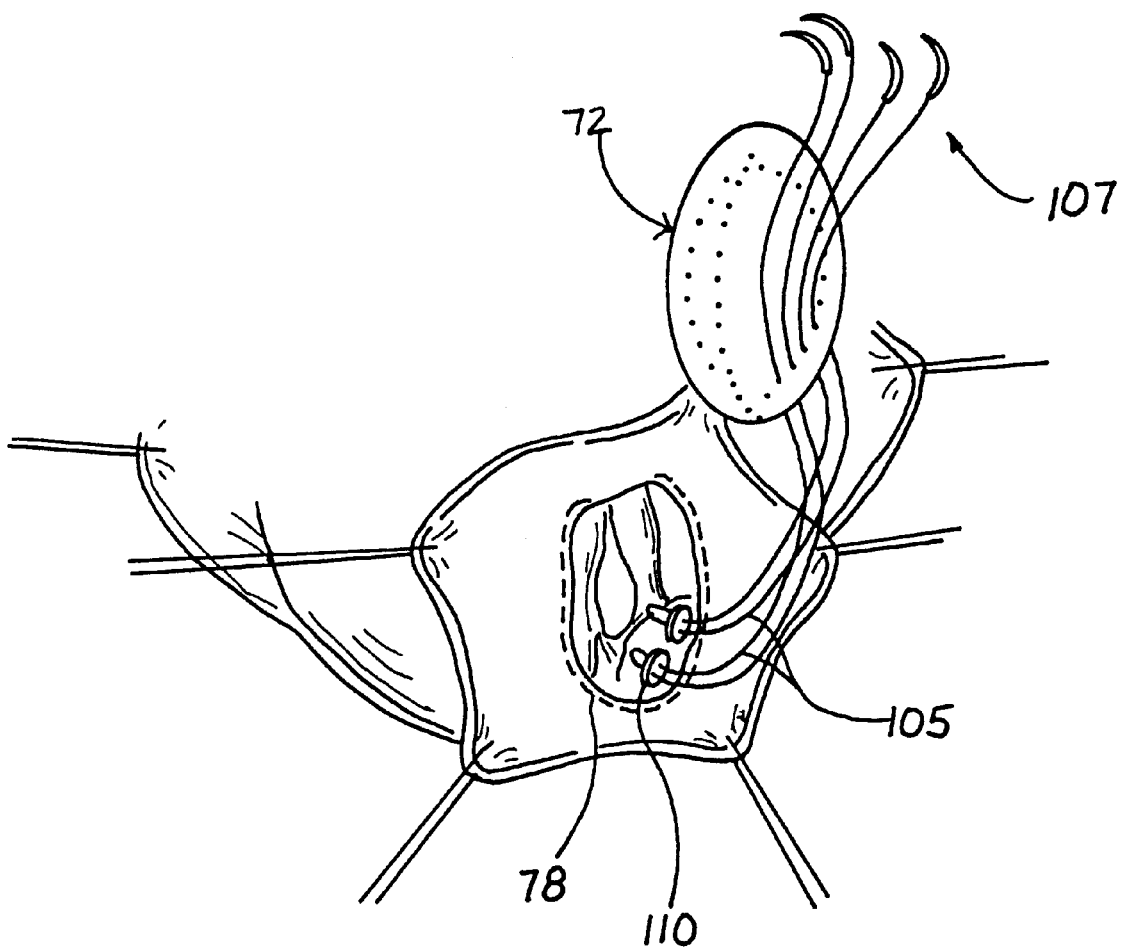
FIG. 21 is an anterior elevation view similar to FIG. 11 and illustrating the placement of pledgeted, interrupted sutures engaging the patch in a remote location.

In a preferred method for placing the patch 72, interrupted sutures 105 can be threaded through the Fontan neck 78 as illustrated in FIG. 21. Where the tissue is soft, the sutures 105 can be looped through pledgets 110 on the interior side of the neck 78 with the free ends of the sutures 105 extending through the exterior side of the neck 78. These free ends, emanating from progressive positions around the circumferential neck 78, are passed incomplementary positions through the body of the patch 72 which is initially positioned remotely of the neck 78 as illustrated in FIG. 21. Since the Fontan stitch 74 may be applied to normal (although akinetic) tissue, the pledgets 110 are preferred to insure that the sutures 105 are well anchored in the neck 78.

Figure 22B:
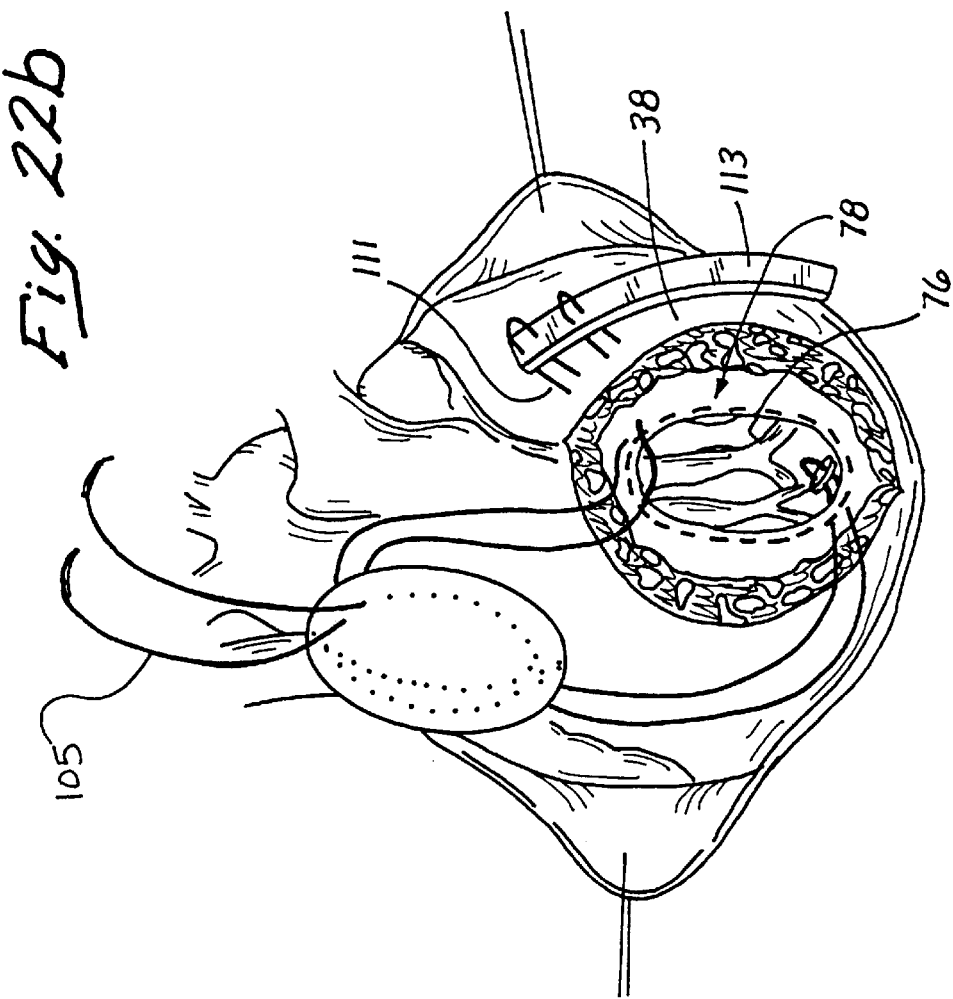
FIG. 22B is a perspective view similar to FIG. 21 and illustrating an alternative method for placement of interrupted sutures.
Figure 22A:
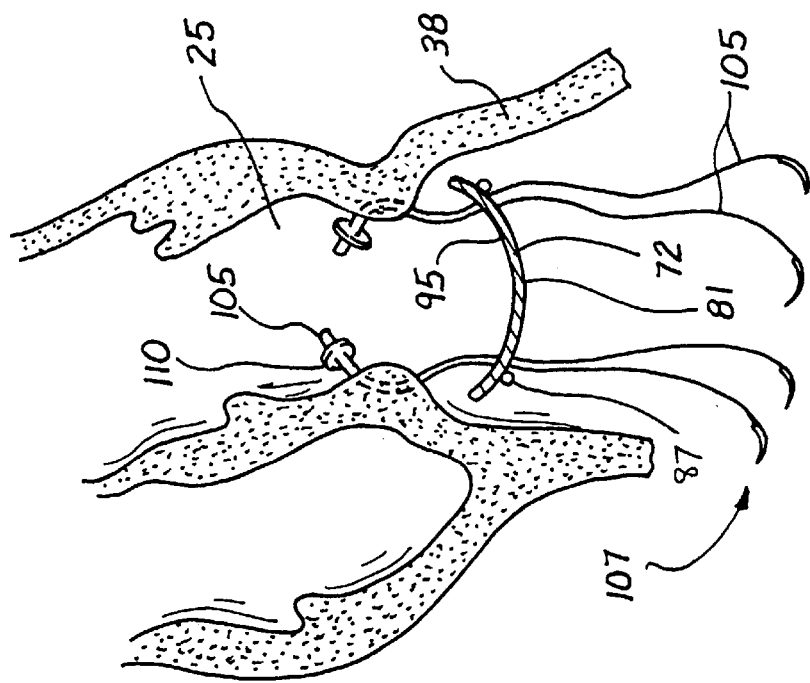
FIG. 22A is an axial cross section view of the left ventricle illustrating the patch being moved along the interrupted sutures from the remote location to the Fontan neck.

Another method for placement of the interrupted patch suture is illustrated in FIG. 22A. In this view, which is similar to FIG. 21, interrupted sutures 111 are directed through the entire ventricular wall 38 and exit the wall 38 in proximity to the protrusion 76 which forms the Fontan neck 78. These sutures 111 can also be anchored in a pledged strip 113 disposed on the outer surface of the heart 12 to further enhance the anchoring of these sutures 111.

Figure 23:
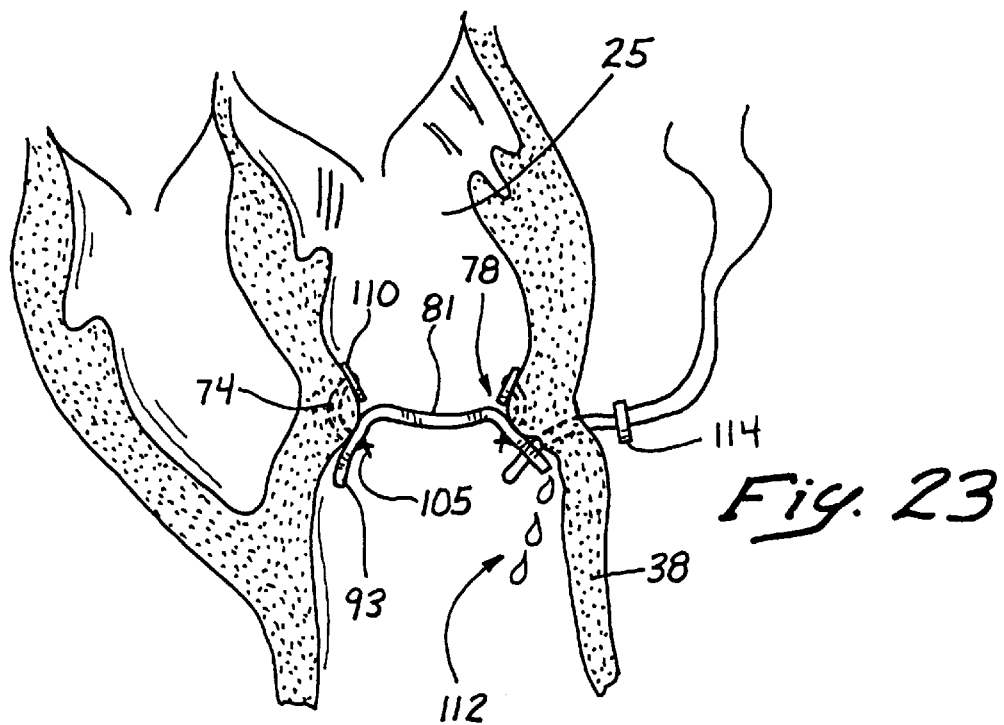
FIG. 23 is an axial cross section view similar to FIG. 22 and illustrating the patch in its final disposition against the Fontan neck, and further illustrating use of the hemostatic rim to control bleeding.

When all of the interrupted sutures 105 have been placed around the circumference of the neck 87, the patch 72 can be moved from its remote location along the sutures 105 and into proximity with the oval neck 78. This step is illustrated in FIG. 22A where the patch 72 is embodied with the concave surface 90 facing the neck 78 and with the ring 87 disposed outwardly of the material 81. After the patch 72 has been moved into an abutting relationship with the neck 78, the interrupted sutures 105 can be tied as illustrated in FIG. 23.

Having closed the left ventricular cavity 25 with the patch 72, one may proceed to address any bleeding which may have resulted from placement of the Fontan stitch 74 or the sutures 105. Such bleeding is illustrated by the reference numeral 112 in FIG. 23. This bleeding 112 will typically occur in close proximity to the neck 78 and beneath the region covered by the rim or flange 93 associated with the material 81 of the patch 72. This bleeding can normally be stopped by merely placing a suture through the ventricular wall 38 and the rim 93 at the point of bleeding. A pledget 114 can be used to tie the suture 112 with the rim 93 closely held against the bleeding wall 38. This reinforcing stitch, acting in combination with the rim 93 of the patch 72, will usually stop any bleeding associated with the sutures.

Figure 24:
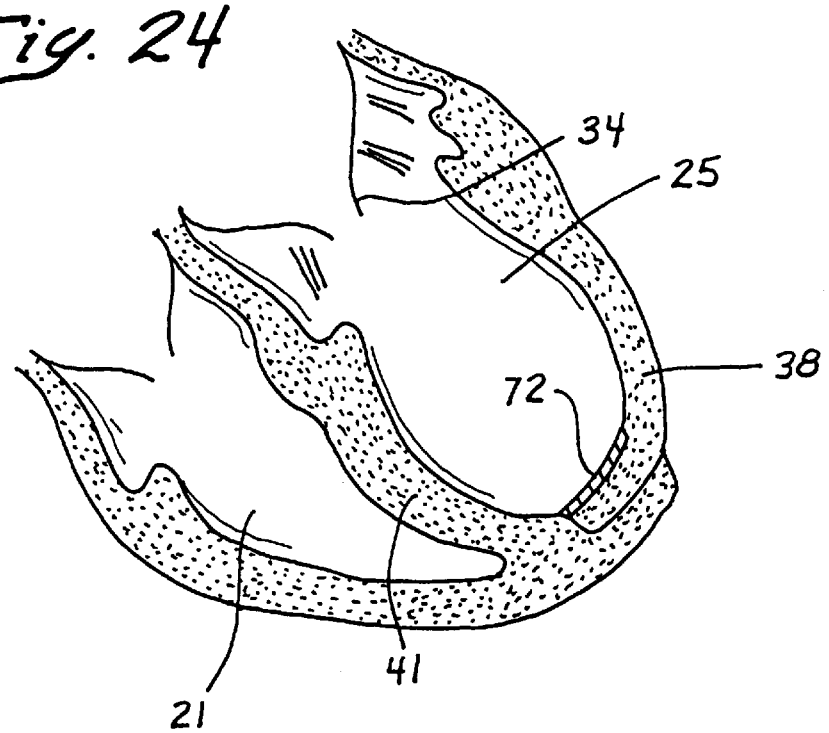
FIG. 24 is an axial cross section view of the ventricular portion of the heart, with the patch mounted in place, the ventricle wall restored to its apical configuration, and the lateral ventricular wall closed in overlapping relationship with the septum wall next to the patch.

With the patch 72 suitably placed, the operative site can be closed by joining the myocardial walls in a vest-over-pants relationship as illustrated in FIG. 24. Care should be taken not to distort the right ventricle 21 by folding the septum wall 41 over the ventricular wall 38. Alternatively, the lateral wall 38 can be disposed interiorly of the septum wall 41 so a majority of the force on the patch 72 is diverted to the lateral wall 38. These walls 38 and 41 can be overlapped in close proximity to the patch 72 in order to avoid creating any cavity between the patch 72 and the walls 38, 41. When air evacuation is confirmed by transesophageal echo, the patient can be weaned off bypass usually with minimal, if any, inotropic support. Decanulasation and closure is routine.

FIG. 24 is positioned in proximity to FIG. 3 in order to illustrate the dramatic difference between the pre-operative dilated heart of FIG. 3 and the post-operative apical heart of FIG. 24. For comparison it will again be noted that the dilated heart of FIG. 3 might typically have a left ventricular volume of 140 milliliters which might produce a blood flow of 42 milliliters with an ejection fraction of 30%. Comparing this with the postoperative heart of FIG. 24, it can be seen initially that the ventricular volume is reduced for example to 90 milliliters. The percentage of viable heart wall as opposed to aldnetic heart wall is greatly increased thereby providing an increase in the ejection fraction, for example from thirty percent to forty-five percent. This combination results in a pumped blood volume of about 40 milliliters with each beat of the heart 12.

These structural changes are somewhat quantitative in consideration. But a further advantage, qualitative in nature, is also associated with the present procedure. It will be noted that this restorative procedure provides the heart 12 with a more natural apical configuration which facilitates the writhing action discussed with reference to the arrow 47 in FIG. 1. Thus, not only is the normal size of the heart achieved, but the restoration procedure also achieves a normal heart operation. In combination, the patch 72 and the resulting procedure significantly reduce the long term effects of myocardial ischemia and overcome many of the causes associated with congestive heart failure.

It may be found that muscle function will be restored to some remote areas following the altered ventricular architecture. Although not fully understood, it is believed that this restoration procedure improves remote segmental myocardial contractibility by reducing the wall tension and stress in the myocardium due to a reduction in ventricular volume. The stress equation states that $$\text{Stress} = \frac{P \times R}{2h}$$

where
P is blood pressure;
R is radius of the heart wall; and
h is wall thickness.

Reducing the ventricular volume decreases the radius, increases the thickness, and thereby reduces wall stress. This improves the myocardial oxygen supply/demand relationship, but may also revive the contractibility of otherwise normal but previously stressed myocardium. At the very least, the reduced stress on the heart 12 is relieved along with any potential for congestive heart failure.

A further advantages of this procedure relates to the incision 61 in the left ventricle 25 which also provides access to the mitral valve 34. Replacing this mitral valve 34 through the left ventricle 25 is much simpler than the present intra-atrial replacement procedure. Coronary artery bypass grafts also can be more easily accommodated intraoperatively. As a result, all of these repairs can be undertaken with greater simplicity and reduced time. While blood cardioplegia may be advantageously used for revascularization and valvular procedures, it would appear that the restorative procedure is best accomplished with continuous profusion of the beating open heart for cardiac protection.

Placement of patch 70 can be further enhanced by providing in the patch kit a plurality of sizing disks which can be individually held in proximity to the Fontan neck in order to determine appropriate patch size. The disks might have a generally planar configuration, and of course, would vary in size. Each disk night have a centrally located handle extending from the planar disk for ease of use. The patch 72 could be removably mounted on a holder also including a disk, on which the patch is mounted, and an elongate handle extending from the disk to facilitate placement.

As further support for the restoration procedure, a special suture needle is contemplated which has a proximal end and a distal end. The proximal end is generally straight and accounts for more than half of the length of the needle. The distal end is curved along a relatively large radius facilitating initial penetration of the thick heart wall. With this configuration, the needle can be easily introduced through the thick myocardium, but then pulled along a generally straight path as it is removed interiorly of the ventricle.

The goal of this procedure is to restore the heart 12 to its normal size, shape and function. This includes restoring the conical apex of the heart in order to achieve the writhing pumping action. The nonfunctioning segmental ventricular myocardium is excluded and replaced with a patch so that the only akinetic wall of the ventricle is that defined by the small patch area. Not only is visual assessment enhanced, but more importantly, palpation affords the surgeon the ability to carefully and accurately determine the circumferential line of separation between the contracting and non-contracting muscle. This determination is achieved although the muscle may have normal color and may not contain either circular or trabecular scar tissue.

It is believed that cardioplegia arrest may be deleterious to ventricular function in the open ventricle because of nonuniform flow distribution. By avoiding this cardioplegia arrest and operating on a beating heart, aortic cross clamping as well as the use of inter-aortic balloons and ventricular assist devices can be avoided. Patch placement can be intraoperatively adjusted guided by echo or radio nucleotide data. Placement of the patch is further simplified by creation of the Fontan neck 78 and use of interrupted felt or pericardial pledgeted sutures 105. The circumferential rim 93 associated with the patch 72 facilitates bleeding control without distortion of the patch 72. Finally, using a vest-over-pants closure of the excluded ventricle obliterates dead space and provides security against patch leaks and resultant expansion.

Within these wide objectives and parameters, there will be variations on the structure of the patch and the methods of restoration. Although the non-circular configuration of the sheet material and ring are believed to be critical, the shape of the patch 72 may vary widely to provide the best anatomical fit with the natural shape of the ventricle 25. The sheet material 81may be composed of a variety of materials, both natural and artificial. These materials may be woven or nonwoven to achieve a desired structure for the sheet material 81. The ring 87 may similarly be formed from a variety of materials and provided with a variety of shapes in order to add structure to the patch 72 without interfering with the normal contractions of the heart 12. Variations of the steps of the associated restoration method might include mounting the patch with a convex surface facing the ventricular cavity, use of tissue adhesives are also contemplated for attaching sealing and otherwise fixing the patch 72 to the Fontan neck 78.

Given these wide variations, which are all within the scope of this concept, one is cautioned not to restrict the invention to the embodiments which have been specifically disclosed and illustrated, but rather encouraged to determine the scope of the invention only with reference to the following claims.

I claim:

1. A method for changing the configuration of a patient's heart, including:
   providing a patch including a non-circular ring adapted to enhance the general conformance of the ring to the natural shape of the left ventricle as the heart beats;
   reducing the volume of the left ventricle using the patch within the heart.

2. The method recited in claim 1, wherein the patient's heart has a left ventricle wall including a healthy portion and a diseased portion divided generally by a zone of separation, and the method further comprises the steps of:
   determining the zone of separation;
   during the reducing step, attaching the patch to the zone of separation with the patch extending across the left ventricle to reduce the volume of the left ventricle.

3. The method recited in claim 2, further comprising the step of:
   during the determining step, determining the zone of separation in response to tactile feedback from the heart.

4. The method recited in claim 2, further comprising the steps of:
   creating an annular protrusion generally around the zone of separation; and
   attaching the patch to the ventricular wall in proximity to the annular protrusion.

5. The method recited in claim 4, wherein the annular protrusion has a first side facing the healthy portion of the wall and a second side facing the diseased portion of the wall, the method further comprising the step of:

during the attaching step, suturing the patch to the second side of the annular protrusion.

6. A method for changing the architecture of a left ventricle of a patient's heart, the ventricle including a wall having first healthy portions and second diseased portions divided by a zone of separation, the method including the steps of:

determining the zone of separation by palpating the wall of the heart when the heart is beating; and inserting a patch into the ventricle to extend generally across the zone of separation.

7. The method recited in claim 6, wherein the determining step includes the step of:

engaging the wall of the ventricle to sense the tactile feedback generated by the beating heart.

8. The method recited in claim 7, wherein the engaging step includes the step of:

engaging the wall of the ventricle between a pair of fingers to sense the tactile feedback of the beating heart.

9. The method recited in claim 7, wherein the inserting step includes the steps of:

providing a patch having a semi-rigid ring with a non-circular shape approaching the anatomical cross-section of the ventricle wall at the zone of separation.

10. The method recited in claim 9, wherein the providing step includes the step of forming the patch from a material including pericardium.

11. A method recited in claim 6, wherein subsequent to the determining step and prior to the inserting step, the method fuither comprises the step of:

fonning an annular protrusion in the ventricular wall generally around the zone of separation.

12. The method recited in claim 10, wherein after the inserting step, the method further comprises the step of suturing the patch to the ventricular wall in proximity to the annular protrusion.

* * * * *

UNITED STATES PATENT AND TRADEMARK OFFICE
CERTIFICATE OF CORRECTION

PATENT NO. : 6,024,096
DATED : February 15, 2000
INVENTOR(S) :
Gerald D. Buckberg; Constantine L. Athanasuleas It is certified that error appears in the above-identified patent and that said Letters Patent is hereby corrected as shown below:

Title Page, item [76]

Inventor: Gerald D. Buckberg, 13238 Riviera Ranch Rd., Los Angeles, Calif. 90049.

Constantine L. Athanasuleas, 1032 Greymoor Road, Birmingham, Alabama 35242

The following Assignee information should appear on the face of the patent:

Assignee: CorRestore, Inc.
100 UCLA Medical Plaza, Box 13
Los Angeles, California 90024

Signed and Sealed this

Twelfth Day of September, 2000

Attest:

Attesting Officer

Q. TODD DICKINSON

Director of Patents and Trademarks

UNITED STATES PATENT AND TRADEMARK OFFICE
CERTIFICATE OF CORRECTION

PATENT NO. : 6,024,096
DATED : February 15, 2000
INVENTOR(S) : Gerald D. Buckberg and Constantine L. Athanasuleas It is certified that error appears in the above-identified patent and that said Letters Patent is hereby corrected as shown below:

<u>Title page,</u>
Item [76], the inventor information should be corrected to read as follows:
-- Inventor: Gerald D. Buckberg, 13238 Riviera Ranch Rd.,
Los Angeles, Calif. 90049

Constantine L. Athanasuleas, 1032 Greymoor Road,
Birmingham, Alabama 35242 --.

Item [73], insert the following Assignee information:
-- Assignee: CorRestore, Inc.
100 UCLA Medical Plaza, Box 13
Los Angeles, California 90024

Signed and Sealed this

Twenty-third Day of July, 2002

*Attest:*

*Attesting Officer*

JAMES E. ROGAN
*Director of the United States Patent and Trademark Office*